(12) United States Patent
Stoll et al.

(10) Patent No.: US 6,985,869 B1
(45) Date of Patent: Jan. 10, 2006

(54) DIGITAL PRESCRIPTION CARRIER AND MONITOR SYSTEM

(75) Inventors: Thomas G. Stoll, Lenexa, KS (US); Karl P. Schmidt, Lawrence, KS (US)

(73) Assignee: NextMed, LLC, Kansas City, MO (US)

( * ) Notice: Subject to any disclaimer, the term of this patent is extended or adjusted under 35 U.S.C. 154(b) by 485 days.

(21) Appl. No.: 09/489,982

(22) Filed: Jan. 21, 2000

(51) Int. Cl.
 G06F 17/60 (2006.01)
 G04G 7/00 (2006.01)
 A61B 5/00 (2006.01)

(52) U.S. Cl. ............... 705/2; 600/301; 702/177
(58) Field of Classification Search ........... 705/2–3; 702/177; 340/309.3, 4, 15; 221/3; 380/30; 600/300–301; 368/10
See application file for complete search history.

(56) References Cited

U.S. PATENT DOCUMENTS

| | | | |
|---|---|---|---|
| 4,200,770 A | 4/1980 | Hellman et al. ............ 380/30 |
| 4,258,354 A | 3/1981 | Carmon et al. .......... 340/309.3 |
| 4,293,845 A | 10/1981 | Villa-Real ............... 340/309.3 |
| 4,504,153 A | 3/1985 | Schollmeyer et al. ......... 368/10 |
| 4,616,316 A * | 10/1986 | Hanpeter et al. ............. 221/2 |
| 4,682,299 A * | 7/1987 | McIntosh et al. .......... 702/177 |
| 4,695,954 A * | 9/1987 | Rose et al. ............... 221/15 |
| 4,835,372 A * | 5/1989 | Gombrich et al. .......... 235/375 |
| 4,837,719 A | 6/1989 | McIntosh et al. .......... 702/177 |
| 4,857,716 A * | 8/1989 | Gombrich et al. .......... 235/375 |
| 4,916,441 A * | 4/1990 | Gombrich ................. 345/169 |
| 4,962,491 A | 10/1990 | Schaeffer ................ 368/21 |
| 5,012,229 A | 4/1991 | Lennon et al. .............. 345/1.1 |
| 5,088,056 A | 2/1992 | McIntosh et al. .......... 702/177 |
| 5,097,429 A | 3/1992 | Wood et al. .............. 702/177 |
| 5,289,157 A | 2/1994 | Rudick et al. .......... 340/309.15 |
| 5,408,443 A | 4/1995 | Weinberger ............... 368/10 |
| 5,495,961 A | 3/1996 | Maestre ................... 221/3 |
| 5,537,475 A | 7/1996 | Micali ................... 380/30 |
| 5,554,967 A | 9/1996 | Cook et al. .......... 340/309.15 |
| 5,602,802 A * | 2/1997 | Leigh-Spencer et al. ...... 368/10 |
| 5,623,242 A * | 4/1997 | Dawson, Jr. et al. ........ 340/7.3 |
| 5,691,932 A | 11/1997 | Reiner et al. ............. 368/10 |
| 5,737,539 A * | 4/1998 | Edelson et al. ............. 705/3 |

(Continued)

FOREIGN PATENT DOCUMENTS

JP 08055174 A * 2/1996

OTHER PUBLICATIONS

Computer Science and Telecommunications Board, For the Record, National Academy Press, Jul. 1997, pp. 12, 86-89, 106-108, anf 120-122.*

(Continued)

Primary Examiner—Joseph Thomas
Assistant Examiner—Carolyn Bleck
(74) Attorney, Agent, or Firm—David E. Herron, II

(57) ABSTRACT

A digital prescription carrier and monitor system includes a pager sized carrier apparatus with an internal processor, a real-time clock/calendar, non-volatile memory, a communication port, a character display, and alert devices. Prescription data for one or more medications is stored within the carrier by a physician and downloaded by a pharmacist to fill the prescriptions called for. The carrier apparatus requires the entry of an decryption key to access prescription data within the carrier to prevent unauthorized access or tampering with the prescription data. The carrier apparatus also functions as a prescription reminder to the patient and records compliance with the prescription, since a switch must be operated to quiet an alert device activated when a scheduled medication dose is due.

21 Claims, 3 Drawing Sheets

U.S. PATENT DOCUMENTS

| | | | |
|---|---|---|---|
| 5,758,095 A * | 5/1998 | Albaum et al. ................. | 705/2 |
| 5,805,051 A * | 9/1998 | Herrmann et al. ....... | 340/309.4 |
| 5,845,255 A * | 12/1998 | Mayaud .......................... | 705/3 |
| 5,876,926 A * | 3/1999 | Beecham ........................ | 435/5 |
| 5,995,939 A * | 11/1999 | Berman et al. ................. | 705/3 |
| 6,018,289 A * | 1/2000 | Sekura et al. ............ | 340/309.4 |
| 6,075,755 A | 6/2000 | Zarchan ........................ | 368/10 |
| 6,294,999 B1 * | 9/2001 | Yarin et al. .............. | 340/573.1 |
| 6,314,384 B1 * | 11/2001 | Goetz .......................... | 702/177 |
| 6,335,907 B1 * | 1/2002 | Momich et al. .............. | 368/10 |
| 6,397,190 B1 * | 5/2002 | Goetz ............................ | 705/3 |
| 6,408,330 B1 * | 6/2002 | DeLaHuerga ................ | 709/217 |
| 6,421,650 B1 * | 7/2002 | Goetz et al. ................... | 705/3 |
| 6,435,175 B1 * | 8/2002 | Stenzler ................. | 128/200.14 |
| 6,438,451 B1 * | 8/2002 | Lion ........................ | 700/237 |

OTHER PUBLICATIONS

Smith, E. and J.H.P. Eloff, Security in health-care information systems—current trends, accepted Oct. 20, 1998, published 1999, International Journal of Medical Informatics, pp. 39-54.*

* cited by examiner

DIGITAL PRESCRIPTION CARRIER AND MONITOR SYSTEM

BACKGROUND OF THE INVENTION

Other than surgery, non-invasive manipulation, and nutrition, the major means of treating diseases and medical conditions is by the use of prescribed and over-the-counter drugs. Drugs which can be harmful if misused or abused are usually required by regulation to be prescribed by a licensed physician and dispensed by a licensed pharmacist.

A prescription is conventionally a written order or "script" by a physician identifying the medication to be dispensed, the dosage, and the time interval at which the dosage is to be taken, or applied in the case of a topical drug. The identity of the drug may include the brand name or its pharmaceutical equivalent. Dosage may include the concentration or the weight of the tablet or capsule containing the active ingredient and may include special instructions, such as before or after meals, before bedtime, or the like. A total number of dosage units is sometimes factored into the dosage for a given medication. In general, prescriptions are intended to achieve and maintain a desired concentration of a drug within a patient for a selected length of time to treat a medical condition.

One problem with the conventional manner of prescriptions is that they are handwritten on a slip of paper. Although errors in filling prescriptions because of legibility problems are rare, they can occur with potentially serious consequences. A conscientious pharmacist will call the prescribing physician if there are any doubts about the prescription script. Another potential problem is that prescriptions can be counterfeited by use of a physician's prescription forms. This usually occurs only with drugs having an abuse or addiction potential. Another problem is that the benefit of a prescribed drug can be diminished if the patient does not follow the prescribed schedule in taking it.

Electronic prescription reminder devices which are programmed with the prescription schedule of one or more drugs are known. Such a device sounds an alarm when it is time to take a medication according to the schedule. Also known are devices which record compliance by the patient in taking a prescription. However, the problems in clearly conveying the prescription information to the pharmacist and prevention of counterfeiting or tampering with prescriptions are not addressed by these devices.

SUMMARY OF THE INVENTION

The present invention provides a method and a prescription carrier apparatus for storing prescription data by a physician and for retrieval by a pharmacist. The carrier data cannot be accessed by the patient; however, the carrier also functions as a prescription reminder for the patient and as a prescription compliance recorder.

The prescription carrier is a device roughly the size of a paging receiver or pager and has a dot matrix liquid crystal display (LCD), an infrared (1R) communications interface, pushbutton keys, a sound alert, and a vibration alert. Internally, the carrier includes a microprocessor, non-volatile memory, a real-time clock/calendar, and interface circuitry to the LCD display, the IR transmit/receive devices, the keys, and the alert devices.

Data access to the prescription carrier is made by way of the IR interface which includes IR receiver and transmitter devices. Such IR interfaces are provided on some laptop computers for communication functions, such as conveying data to be printed to a printer without electrical connection of the laptop to the printer. The IR interface provides for communication with a physician's computer or a pharmacist's computer, both of which are provided with appropriate software to respectively upload or download prescription and/or compliance data. The prescription data may be in the form of a data record with data fields which can be parsed by software within the prescription carrier to retrieve the name of the medication along with dosage factors and dosage scheduling. The processor within the carrier uses the dosage scheduling data to set up a prescription reminder schedule for each medication in cooperation with the real time clock/calendar and the alert devices. By this means, the carrier alerts the patient each time a dose of the prescription medication is due.

The prescription carrier includes a "delay" switch and a "take" switch. The delay switch functions similar to a "snooze" button on a conventional alarm clock. It initiates a delay clock function to alert again at the end of a delay period, for example, of ten or fifteen minutes. Some prescriptions may not allow delays in taking a dose. The take switch is operated when the patient takes a medication upon being alerted to do so and also deactivates the alert device. While operation of the delay switch is not generally recorded, operation of the take switch is recorded as a "compliance" with the prescription. Each compliance record may include the identity of the medication and the time and date that the take switch was operated. The compliance data can be downloaded by the prescribing physician to compare treatment progress with prescription compliance or to simply determine if the patient has or has not been taking the medication as prescribed.

Because allowing the patient access to data within the prescription carrier could result in obvious problems, such access is restricted to the prescribing physician and the pharmacist, or their employees. Access can be restricted by the use of simple passwords. However, the data within the prescription carrier of the present invention is preferably encrypted using one or more encryption keys or digital signatures which are available only to the physician and the pharmacist, but not to the patient. The sciences of effective techniques for encryption of digital data and encryption keys for decrypting are well developed. Background information on such encryption and digital signature techniques can be obtained from U.S. Pat. Nos. 4,200,770 and 5,537,475, which are incorporated herein by reference. If the present invention, digital signatures incorporating license numbers issued by the U.S. Drug Enforcement Agency (DEA) are preferred.

Objects and Advantages of the Invention

The principal objects of the present invention are: to provide an improved method and apparatus for conveying a prescription medication from a physician to a patient; to provide such a system including a portable prescription carrier apparatus in which data representing the prescription is uploaded by a physician and downloaded by a pharmacist to fill the prescription; to provide such a prescription carrier apparatus including circuitry and logic which is programmable with prescription data including a prescription schedule for alerting a patient when a dose of a medication is due; to provide such a carrier apparatus which is operable to record compliance of the patient with the prescription for subsequent downloading and analysis by the prescribing physician; to provide such a carrier apparatus which is similar in size and shape to a pager receiver and which includes both sonic and vibratory alert devices; to provide such a carrier apparatus in which prescription data therein is encrypted and which cannot be decrypted by the patient to thereby prevent falsification or counterfeiting of the prescription data therein; and to provide such a digital prescription carrier and monitor system which is economical to manufacture, which is precise and effective in use, and which is particularly well adapted for its intended purpose.

Other objects and advantages of this invention will become apparent from the following description taken in conjunction with the accompanying drawings wherein are set forth, by way of illustration and example, certain embodiments of this invention.

The drawings constitute a part of this specification and include exemplary embodiments of the present invention and illustrate various objects and features thereof.

DETAILED DESCRIPTION OF THE INVENTION

Figure 1:
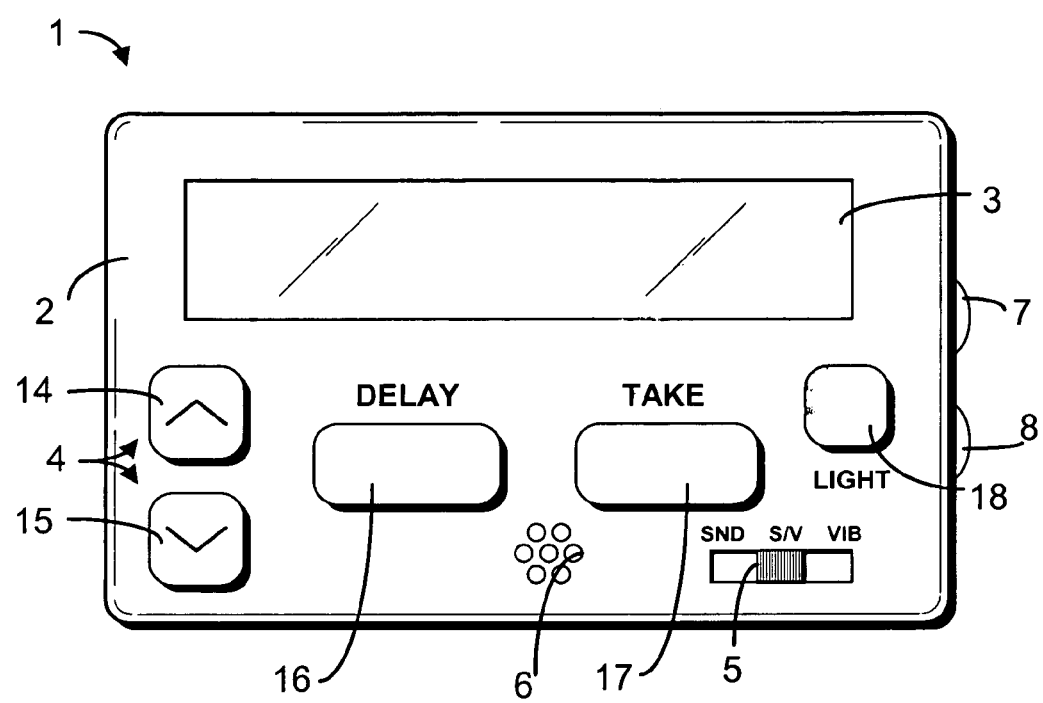
FIG. 1 is a front elevational view of a digital prescription carrier and monitor system which embodies the present invention.

As required, detailed embodiments of the present invention are disclosed herein; however, it is to be understood that the disclosed embodiments are merely exemplary of the invention, which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Referring to the drawings in more detail:

The reference numeral 1 generally designates a digital prescription carrier and monitor device which embodies the present invention. In general, the carrier 1 is adapted to have prescription data uploaded thereinto from a physician's computer for transportation to a pharmacy at which the prescription data is downloaded into a pharmacist's computer and the prescription filled. The carrier 1 is also adapted to provide alerts at times when the prescribed medication is to be taken in accordance with the prescription and to record compliance by the patient with the prescription.

Figure 2:
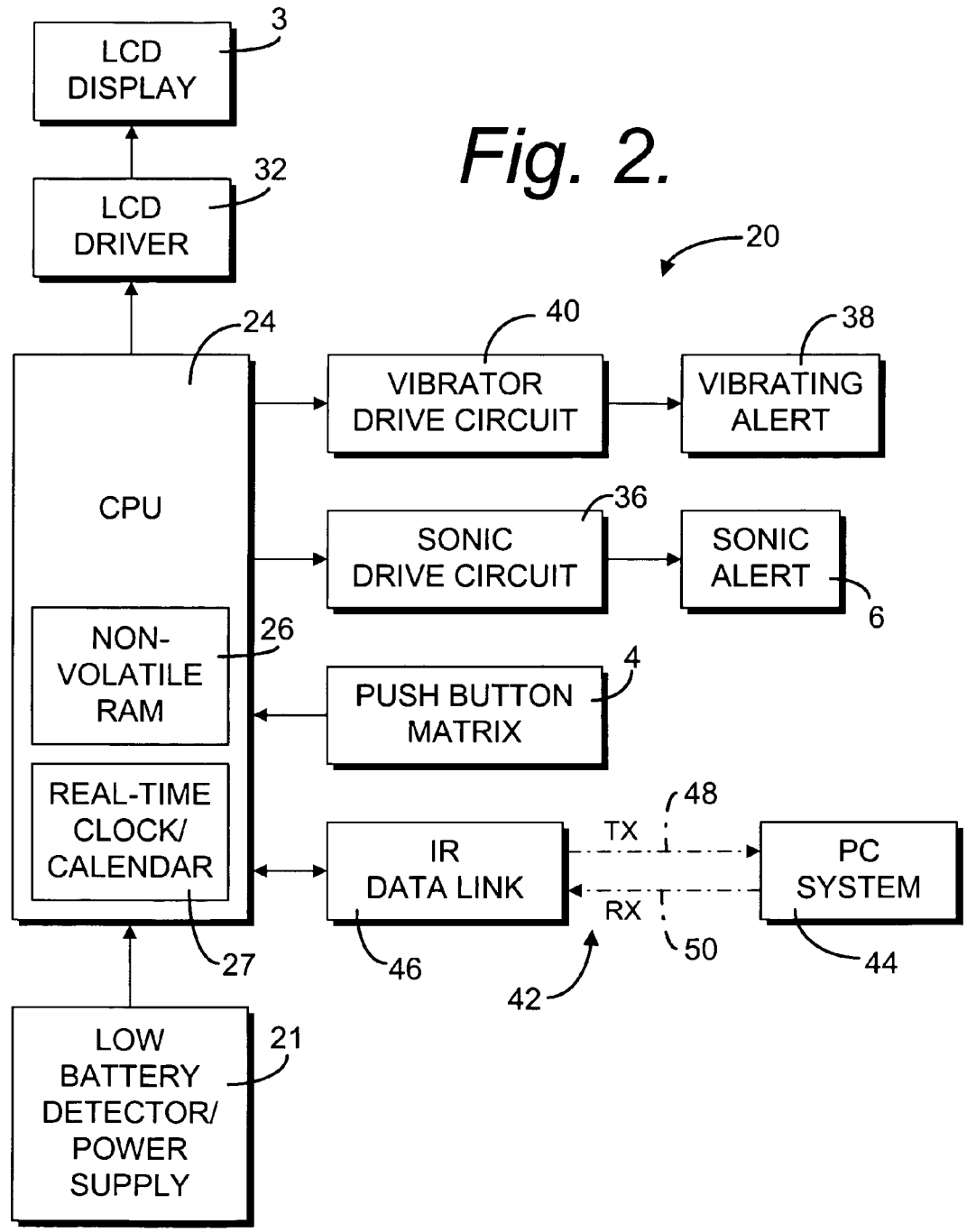
FIG. 2 is a block diagram illustrating the principal circuit components of the digital prescription carrier and monitor system.

The carrier 1 includes an outer housing 2 sized similar to a pager and may include a resilient belt clip (not shown) for wearing the carrier 1 on the belt of a patient or user. The housing 2 includes a dot-matrix liquid crystal display 3, operation buttons 4, an alert device selection switch 5, a sonic output device 6, and infrared interface link windows 7 and 8. The illustrated carrier 1 includes buttons for scrolling up 14, scrolling down 15, delay 16, take 17, and backlight toggle or light 18. The housing 2 also has a battery (not shown) which powers circuitry 20 (FIG. 2) therein through a low battery detector power supply 21.

The circuitry 20 includes a central processing unit or CPU 24 which may be a microprocessor or microcontroller. The processor 24 includes, among other on-chip components, non-volatile RAM memory 26 and a real-time clock/calendar 27. Alternative to, or in addition to, the non-volatile RAM 26, the CPU 24 may include or be interfaced with read-only memory (ROM) and/or conventional memory or RAM (neither shown). Software 30 (FIG. 3) which operates within the carrier 1 is stored in the non-volatile RAM 26.

The operation buttons or switches 4 are interfaced to the CPU 24, as is the LCD display 3. LCD driver circuitry 32 interfaces the display circuitry 3 to the CPU 24. Preferably, the display 3 is a dot-matrix type which provides greater flexibility of characters which can be displayed thereon than, for example, 7-segment type displays. The illustrated display 3 may, for example, be a commonly available 16 character by 2 line display. The illustrated carrier 1 includes the scroll buttons 14 and 15, the delay switch 16, the take switch 17, the backlight switch 18, and the alert select switch 5. However, it is foreseen that other user-selected functions may be desirable in the carrier 1, such that the carrier 1 is not intended to be limited only to the switches shown. The backlight switch 18 toggles one or more light emitting diodes or LED's (not shown) which illuminate the display 3 to facilitate reading the display in darkness. Although the display 3 is preferably formed using liquid crystal display technology because of its low power consumption and ready availability, other display technologies could alternatively be employed.

The carrier 1 is provided with the sonic alert device 6 to remind the user that it is time for a dose of a medication, the schedule for which is being tracked by the carrier 1. The sonic alert device 6 may be a small loudspeaker or other audio transducer capable of generating an acoustic signal. The device 6 is powered by sonic drive circuitry 36 and interfaced to the CPU 24 thereby. The sonic drive circuitry 36 may simply be a power amplifier or may incorporate other elements. The carrier 1 is also preferably provided with a vibrating alert device 38 in cooperation with vibrator drive circuitry 40. Such vibrating alert devices are common in paging receivers and generate a tactile vibration when activated. The alert mode selection switch 5 enables the user to select either the sonic alert 6, the vibrating alert 38, or both. Although not illustrated, it is also foreseen that the carrier 1 could be provided with a flashing lamp as an alternative alert device for hearing impaired persons, although such persons would still benefit from the vibrating alert 38.

The carrier 1 includes a communication port 42 for interfacing the carrier 1 to an external computer or PC system 44. Such a communication port 42 could be a conventional RS-232 serial port or a more recent communication interface such as a universal serial bus (USB) interface, a "Firewire" (trademark of Apple Computer, Inc.) interface, or the like. In the illustrated carrier 1, the communication port 42 is an infrared (IR) data link 46 including a transmitter (TX) channel 48 and a receiver (RX) channel 50. Such IR links 46 are provided on some laptop computers, as well as on some peripheral devices, such as printers, so that a document can be printed from the laptop computer by the printer without a conductive connection. In the carrier 1, the IR port 46 is used to upload a prescription data into the carrier 1 and to download such data from the carrier 1.

Figure 3:
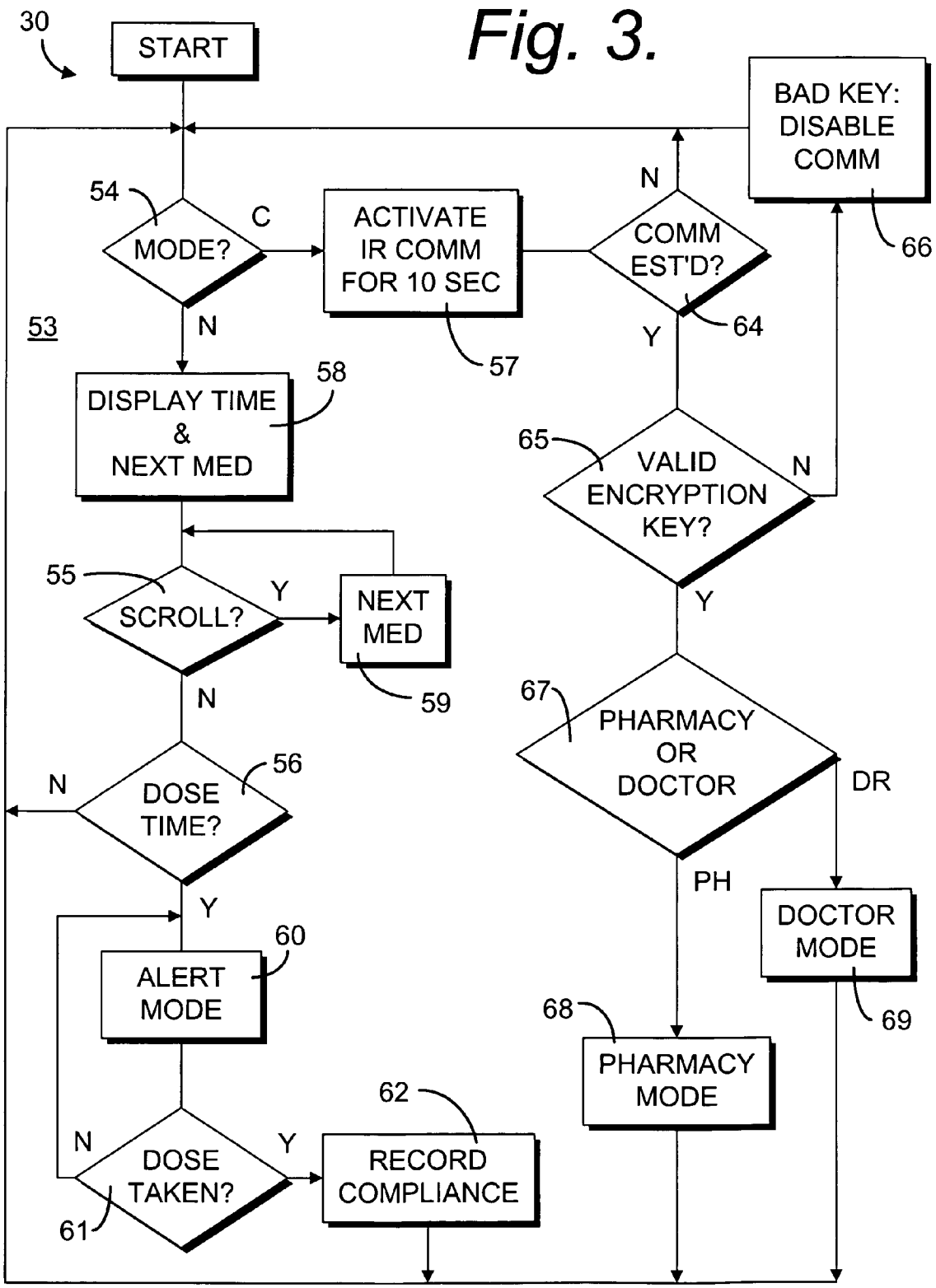
FIG. 3 is a flow diagram illustrating the principal software components of the system.

FIG. 3 illustrates the principal functions of the software 30 which is executed by the CPU 24 of the carrier 1. In general, the carrier 1 is able to track the schedules for a plurality of medications, the number of which is limited by the size of the RAM 26, in cooperation with the real-time clock/calendar 27. When a dose of a medication is due, one or both of the alert devices 6 and/or 38 is activated. The user of the carrier 1 can review the upcoming medication schedule on the display 3 using the scroll keys 14 and 15. The prescription data is entered into the carrier 1 from an external computer 44 and accessed to fill the prescriptions by way of the IR data link 46. The external computer 44 executes special software (not detailed herein) to access the carrier 1.

Referring particularly to FIG. 3, from the start function 52, when a new battery (not shown) is installed in the carrier 1, a main loop 53 is entered. The main loop 53 includes a mode test 54, a scroll test 55, and a dose time test 56. If both scroll keys 14 and 15 are pressed simultaneously, the IR data link 46 is activated at 57 for a selected wait interval, such as 10 seconds. Otherwise, the current time/date is displayed and next scheduled medication to be taken and dose time are displayed, at 58, and the scroll test 55 is entered. If operation of a single scroll key 14 or 15 is detected at 55, the next medication and dose time are displayed at 59. This allows the user to review upcoming medications and schedules by simply scrolling through a list. If no scroll key operation is detected, the CPU 24 checks to determine if a dose of a medication is currently due. If not, the process 30 loops back to the mode test 54.

If a medication dose is due at the dose time test 56, an alert mode 60 is entered. In the alert mode, one or both of the alert devices 6 or 38 is activated, depending on the state of the alert select switch 5. The alert can be delayed somewhat depending on the medication involved, by operation of the delay switch 16. The delay switch 16 causes the carrier 1 to function similar to an alarm clock with a "snooze" feature. At the end of a delay interval, the alert recurs. However, if the take switch 17 is operated, at 61, the alert device 6/38 is deactivated, operation of the take switch 17 is recorded, at 62, as a "compliance" with the prescription, and the time of compliance is recorded by the CPU 24 in the RAM 26. After recording compliance at 62, the CPU 24 returns to the mode test 54.

When the IR data link 46 is activated at 57, a communication test is run at 64. If a communication link has not been established with an external computer 44 by the end of the wait interval, the IR data link 46 is deactivated and control is returned to the mode test 54. If communications have been established at 64, a security test 65 is entered, requiring the entry of a valid encryption key or a password. If the entered encryption key or password is not correct, communication between the carrier 1 and the external computer 44 is disabled at 66 and control is passed to the mode test 54.

If the encryption key or password is valid, a communication mode test 67 is conducted to determine if a pharmacy mode 68 or a doctor mode 69 is to be entered. In the pharmacy mode 68, the pharmacist is allowed to access all the current prescriptions, to decrement refill counts of certain prescriptions, and to view patient information which is stored in the carrier 1. The doctor mode 69 includes all pharmacy mode privileges and additionally allows entry and deletion of prescriptions, entry or update of patient information, and access to prescription compliance data.

Most states still require the presentation of a prescription form signed by a physician for certain medications, especially those with a high potential for abuse. Prescriptions for other drugs may be "called in". The carrier 1 has utility as a sole prescription carrier or as a digital version of a conventional signed prescription form. The digital prescription data stored in the carrier 1 can be uploaded into the pharmacy computer system for inventory control purposes, as well as to reduce data entry errors and for cross-checking purposes. Thus, the carrier 1 of the present invention complements the functions of current paper based methods of filling prescriptions rather than simply replacing or duplicating such functions. The carrier 1 also has a reminder function and a compliance recording functions. The data link 46 gives the carrier 1 the capability of being accessed remotely, for example over the internet, for the entry or modification of prescriptions by the physician or review of the prescriptions or compliance data by the physician or pharmacist.

It is to be understood that while certain forms of the present invention have been illustrated and described herein, it is not to be limited to the specific forms or arrangement of parts described and shown.

The invention claimed is:

1. A method for conveying a prescribed medication to a patient, the method comprising the steps of:
    providing a digital prescription carrier including a read/write memory and an infrared communication interface;
    encrypting prescription data defining a prescription so that the data would be indecipherable without appropriate computer decryption software;
    uploading, by a prescriber, the prescription data into said carrier through said interface, said prescription calling for the use of a selected medication of a selected dosage on a selected schedule;
    transferring said carrier by a patient to a pharmacy;
    downloading said prescription data from said carrier through said interface at said pharmacy;
    decrypting said prescription data from indecipherable form into a form that would be decipherable; and
    filling said prescription at said pharmacy; wherein,
    the uploading and downloading steps are each accomplished by a data transfer that occurs without physical contact.

2. A method as set forth in claim 1, further including the step of entering a first access code into said carrier to enable access to said prescription data prior to said uploading step.

3. A method as set forth in claim 2, further including the step of entering a second access code into said carrier to enable access to said prescription data prior to said downloading step.

4. A method as set forth in claim 2, further including the steps of:
    endowing a prescriber with the first access code;
    updating, by a prescriber, of prescription information including at least one of
        deleting a piece of stored prescription data;
        adding a new piece of stored prescription data;
        changing a piece of stored prescription data;
    endowing the pharmacist with the second access code; and,
    updating, by the pharmacist, of prescription information including at least one of
        noting the filling of a prescription;
        reducing the number of refills remaining for a piece of stored prescription data; or,
        updating patient information.

5. A method as set forth in claim 1, further including the steps of:
    (a) operating a digital clock/calendar within said carrier to generate internal values of time and date;
    (b) providing said carrier with a prescription compliance switch interfaced to said clock/calendar;
    (c) operating said compliance switch by a patient upon taking a medication specified by said prescription; and (d) storing in a compliance memory within said carrier respective values of time and date occurring upon operation of said compliance switch.

6. A method as set fort in claim 5, further including the steps of:
   (a) providing said carrier with an annunciator or element,
   (b) entering into said carrier by said pharmacist schedule data defining a prescription schedule comprising a plurality of sets of schedule times and dates at which a patient is to take a medication specified by prescription;
   (c) periodically comparing within said carrier said internal values of fine and date with said schedule times and dates; and
   (d) activating said annunciator element upon said internal values of time and date matching a set of said schedule time and schedule date.

7. A method as set forth in claim 1, further including the steps of:
   (a) uploading prescription data defining a plurality of prescriptions for a plurality of medications into said carrier through said interface;
   (b) downloading said prescription data through said interface; and
   (c) filling each of said prescriptions defined by said prescription data.

8. A method as set forth in claim 1, further including the step of entering a second access code into said carrier to enable access to said prescription data prior to said downloading step.

9. A method for conveying a prescribed medication to a patient, the method comprising the steps of:
   providing a digital prescription carrier including a read/write memory and a communication interface;
   entering a first access code into said carrier to enable software access thereto;
   uploading prescription data defining a prescription, said data being in a wholly intangible digital form, into said carrier through said interface, said prescription calling for the use of a selected medication of a selected dosage on a selected schedule;
   encrypting said prescription data so that said data would be indecipherable without appropriate computer decryption software;
   transferring said carrier by a patient to a pharmacy;
   entering a second access code into said carrier to enable software access thereto;
   downloading said prescription data, said data being in a wholly intangible digital form, from said carrier through said interface at said pharmacy;
   decrypting the prescription data to convert the data into an intelligible form; and
   filling said prescription by said pharmacist.

10. A method as set forth in claim 9, further including the steps of:
    (a) operating a digital clock/calendar within said carrier to generate internal values of time and date;
    (b) providing said carrier with a prescription compliance switch interfaced to said clock/calendar;
    (c) operating said compliance switch by a patient upon taking a medication specified by said prescription; and
    (d) storing in a compliance memory within said carrier respective values of time and date occurring upon operation of said compliance switch.

11. A method as set forth in claim 10, further including the steps of:
    (a) providing said carrier with an annunciator element;
    (b) entering into said carrier by said pharmacist schedule data defining a prescription schedule comprising a plurality of sets of schedule times and dates at which a patient is to take a medication specified by said prescription;
    (c) periodically comparing within said carrier said internal values of time and date with said schedule times and dates; and
    (d) activating said annunciator element upon said internal values of time and date matching a set of said schedule time and schedule date.

12. A method as set forth in claim 11 wherein said annunciator element includes a vibrating element.

13. A method as set forth in claim 9, wherein said communication interface includes an infrared data communication interface.

14. A method as set forth in claim 7, further including the steps of:
    (a) uploading, by a physician, prescription data defining a plurality of prescriptions for a plurality of medications to be taken on a plurality of schedules into said carrier through said interface;
    (b) downloading, by a pharmacist, said prescription data through said interface; and
    (c) filling each of said prescriptions defined by said prescription data.

15. A method as set forth in claim 9, further including the steps of:
    (a) providing said carrier with an annunciator element;
    (b) enter into said carrier, by said pharmacist for each of said prescriptions, schedule data defining a respective prescription schedule comprising a plural of sets of schedule times and dates at which a patient is to take a medication specified by the respective prescription;
    (c) periodically comparing within said carrier said internal values of time and date with said schedule times and dates; and
    (d) activating said annunciator element upon said internal values of time and date matching a set of said schedule time and date.

16. A digital prescription carrier apparatus comprising:
    a carrier housing;
    a central processing unit (CPU) positioned within said housing;
    a display device positioned on said housing, interfaced to said CPU, and capable of displaying alphanumeric characters;
    input/output (I/O) interface circuitry positioned in said housing and interfaced to said CPU, said I/O circuit being capable of interfacing said CPU to an external computer to exchange data therewith;
    data memory circuitry positioned within said housing;
    encrypting software for scrambling prescription data that represents a prescription into a form that is unintelligible and unreadable, said encrypting software further capable of converting encrypted prescription data to a readable form; and,
    prescription software stored in said memory to be processed by said CPU,
        wherein, the CPU and the I/O circuitry cooperate to enable
        uploading, by a prescriber, of the prescription data into said memory circuitry, and
        downloading of said prescription data at a pharmacy.

17. A digital prescription carrier apparatus as set forth in claim 16, further including:
(a) a real-time clock/calendar positioned within said housing and interfaced to said CPU;
(b) an alert device positioned within said housing and interfaced to said CPU; and
(c) said prescription software cooperating with said prescription data, said clock/calendar, and said alert device to cause activation of said alert device when a dose of medication prescribed by said prescription data is to be taken.

18. A digital prescription carrier apparatus as set forth in claim 17, further including:
(a) a compliance switch positioned on said housing and interfaced to said CPU; and
(b) said prescription software cooperating with said compliance switch to record in said data memory circuitry an occurrence of the operation of said compliance switch subsequent to activation of said alert device.

19. A digital prescription carrier apparatus as set forth in claim 17 wherein said alert device includes at least one of:
(a) a sonic alert device interfaced to said CPU; or
(b) a vibrating alert device interfaced to said CPU.

20. A digital prescription carrier apparatus as set forth in claim 16, further including:
(a) a plurality of key switches positioned on said housing and interfaced to said CPU;
(b) said prescription software causing uploaded prescription data to generate a schedule of dose times for a medication represented by said prescription data; and
(c) operation of said key switches enabling review of said schedule of dose times for said medication in cooperation with said display device.

21. A digital prescription carrier apparatus as set forth in claim 16 wherein said I/O interface circuitry includes an infrared data link.

* * * * *